United States Patent [19]

Sommargren

[11] Patent Number: 4,733,967

[45] Date of Patent: Mar. 29, 1988

[54] APPARATUS FOR THE MEASUREMENT OF THE REFRACTIVE INDEX OF A GAS

[75] Inventor: Gary E. Sommargren, Madison, Conn.

[73] Assignee: Zygo Corporation, Middlefield, Conn.

[21] Appl. No.: 27,644

[22] Filed: Mar. 19, 1987

[51] Int. Cl.⁴ .............................................. G01B 9/02
[52] U.S. Cl. ................................................ 356/361
[58] Field of Search ........................................ 356/361

[56] References Cited

U.S. PATENT DOCUMENTS 4,571,082  2/1986  Downs .......................... 356/361 X
4,685,803  8/1987  Sommargren .................. 356/361

Primary Examiner—Vincent P. McGraw
Assistant Examiner—Matthew W. Koren
Attorney, Agent, or Firm—Stiefel, Gross & Kurland

[57] ABSTRACT

Apparatus capable of measuring either changes in the refractive index, or, if desired, the absolute refractive index, of a gas is provided which comprises a differential plane mirror interferometer to produce a pair of measurement beams and a pair of reference beams; and a gas-tight refractive index cell means (78) comprised, most preferably, of a window (70) affixed to the end of a cylindrical tube (73) closest to the interferometer and a mirror (75) affixed to the other end of the tube (73), the cell (78) being aligned to the interferometer so that the reference beams pass inside of the tube (73) in a sealed volume and the measurement beams pass outside of the tube (73), such as in ambient air, for the measurement of changes in the refractive index of the gas surrounding the gas-tight cell (78). When the absolute refractive index of a gas is to be measured, the gas-tight cell (78) comprises, most preferably, a window (70) affixed to the ends of a pair of cylindrical concentric tubes (73, 86) closest to the interferometer and a mirror (75) affixed to the other ends of the tubes (73, 86) to provide two sealed volumes, with the cell (78) being aligned to the interferometer so that thereference beams pass through the sealed volume of the inner tube (73) of the pair (73, 86) which is evacuated, and the measurement beams pass through the sealed volume between the tubes (73, 86), which sealed volume is either evacuated or contains the gas whose absolute refractive index is to be measured. In both embodiments, means (90, 92) for measuring the phae variation between the reference and measurement beams after they traverse the gas-tight cell (78); and means, most preferably a microcomputer, for converting the measured phase variation to provide an output which is either the changes in or the absolute refractive index of a gas are provided.

35 Claims, 2 Drawing Figures

APPARATUS FOR THE MEASUREMENT OF THE REFRACTIVE INDEX OF A GAS

CROSS-REFERENCE TO RELATED APPLICATIONS

This application is related to my copending U.S. patent application, entitled "Method and Apparatus for the Measurement of the Refractive Index of a Gas," bearing U.S. Ser. No. 821,773, filed Jan. 23, 1986, the contents of which are specifically incorporated by reference herein in its entirety and is an improvement thereon.

BACKGROUND OF THE INVENTION

1. Field of the Invention

The present invention relates to apparatus for the measurement of the refractive index of a gas. More particularly, the invention relates to optical apparatus which is useful for high accuracy displacement metrology using interferometry in ambient air.

2. The Prior Art

An interferometer is the basic instrument for most of the high-accuracy displacement measurements in the machine tool and semiconductor fabrication industries. One type of interferometer representative of the current state-of-the-art is described in Bagley et al., U.S. Pat. No. 3,458,259 issued July 26, 1969. The absolute accuracy of interferometric displacement metrology is limited by two dominant factors: (1) the uncertainty in the vacuum wavelength of the light source, and (2) the uncertainty in the refractive index of the ambient air, see W. Tyler Estler, "High-Accuracy Displacement Interferometry in Air", Applied Optics, Vol. 24, pp. 808–815 (Mar. 15, 1985) and Farrand et al., U.S. Pat. No. 4,215,938 issued Aug. 5, 1980.

As noted in the aforementioned references, interferometric displacement measurements in air are subject to environmental uncertainties, particularly to changes in air pressure, temperature, humidity, and molecular composition. Such factors alter the wavelength of the light used to measure the displacement. Under normal conditions the refractive index of air is approximately 1.0003 with a variation of $\pm 1 \times 10^{-4}$. In many applications the refractive index of air must be known with an arror of less than $10^{-7}$ to $10^{-8}$.

One prior-art technique for correcting the environmental uncertainties is based on using individual sensors to measure the barometric pressure, temperature, and humidity, and, then, using these measurements to correct the measured displacement, see for example, Maeda, U.S. Pat. No. 4,355,894 issued Oct. 26, 1986. The commercially available Automatic Compensator, Model 5510 Opt 010, from Hewlett-Packard uses this technique. This technique has been only partly satisfactory due to the errors in the sensors and due to the errors arising from variations in the composition of the air, e.g., the percentage $CO_2$ content and presence of industrial gases, i.e., Freon and solvents are ignored in this technique.

A second prior-art technique is based on the aforementioned Farrand et al., U.S. Pat. No. 4,215,938 issued Aug. 5, 1980. This technique incorporates a rigid enclosure, the length of which must be accurately known, independent of environmental conditions and constant in time. This technique uses a plane mirror interferometer which itself has a high temperature coefficient and, thusly, is a source of systematic errors.

Another prior-art technique is disclosed in Downs, U.S. Pat. No. 4,571,082 issued Feb. 18, 1986. With this technique the well-known Jamin interferometer is combined with a modern fringe counting technique. However, it suffers from several serious limitations. First, significant parts of the measurement beam feed back directly into the laser thereby causing its frequency to become unstable. Second, it requires an auxiliary lens, retardation plate, and mirror which introduce errors. Third, it has low light efficiency.

Another prior-art technique, which is an absolute refractometer, is disclosed in my copending U.S. patent application, Ser. No. 821,773, entitled "Method and Apparatus for the Measurement of the Refractive Index of a Gas," filed Jan. 23, 1986.

Consequently, while prior-art techniques for measuring the refractive index of a gas are useful for some applications, none known to the applicant provide the technical performance in a commercially viable form for applications requiring the high accuracy interferometric measurement of displacement in air. The disadvantages of the prior-art apparatus are overcome by the present invention.

SUMMARY OF THE INVENTION

In accordance with the instant invention, apparatus capable of measuring either changes in the refractive index, or, if desired, the absolute refractive index, of a gas is provided which comprises a differential plane mirror interferometer to produce a pair of measurement beams and a pair of reference beams; and a gas-tight refractive index cell means comprised, most preferably, of a window affixed to the end of a cylindrical tube closest to the interferometer and a mirror affixed to the other end of the tube, the cell being aligned to the interferometer so that the reference beams pass inside of the tube in a sealed volume and the measurement beams pass outside of the tube, such as in ambient air, for the measurement of changes in the refractive index of the gas surrounding the cell; or a gas-tight refractive index cell comprised, most preferably, a window affixed to the ends of a pair of cylindrical concentric tubes closest to the interferometer and a mirror affixed to the other ends of the tubes to provide two sealed volumes, with the refractive index cell being aligned to the interferometer so that the reference beams pass through sealed volume of the inner tube of the pair which is evacuated, and the measurement beams pass through the sealed volume between the tubes, which sealed volume is either evacuated or contains the gas whose absolute refractive index is to be measured; and in both embodiments, means for measuring the phase variation between the reference and measurement beams after they traverse the refractive index cell; and means, most preferably a microcomputer, for converting the measured phase variation to provide an output which is either the changes in or the absolute refractive index of a gas are provided.

THE DRAWINGS

FIG. 1 depicts in schematic form one embodiment of the apparatus of the instant invention where all the optical beams are in a single plane; and FIG. 2 depicts in schematic form a second embodiment of the apparatus of the instant invention configured to measure the absolute refractive index of a gas.

DETAILED DESCRIPTION OF THE INVENTION

Figure 1:
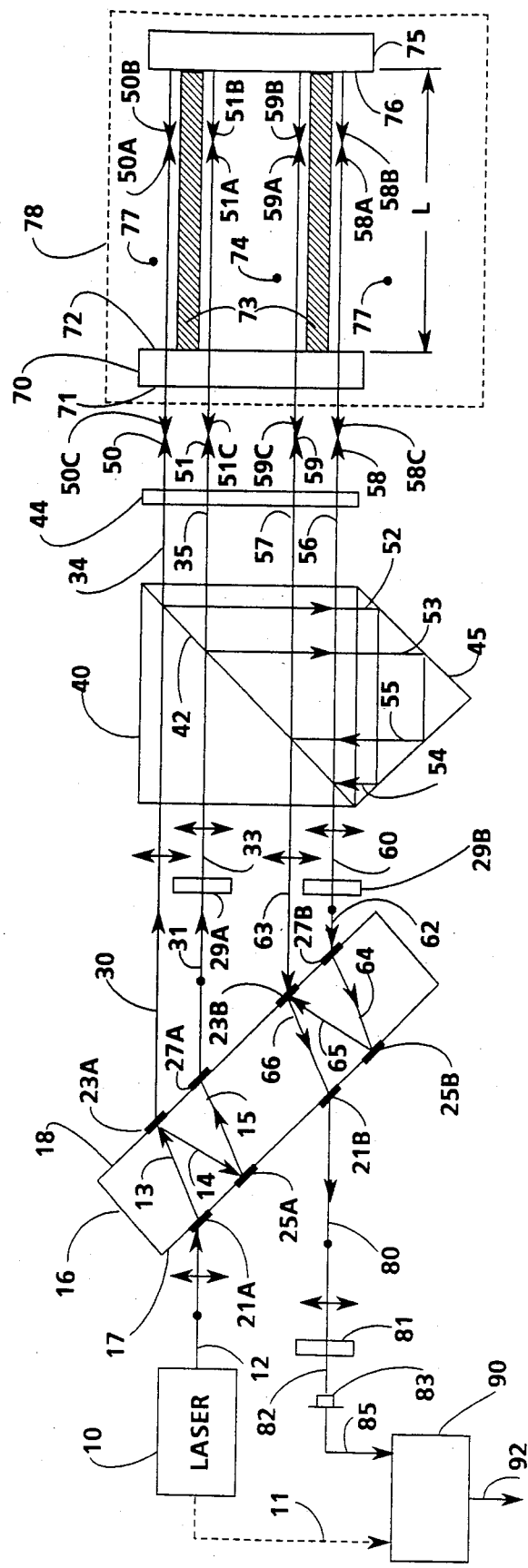

FIG. 1 depicts in schematic form one embodiment of the apparatus of the instant invention where all the optical beams are in a single plane. While the apparatus has application for a wide range of radiation sources, the following description is taken by way of example with respect to an optical measuring system. Light source (10), which most preferably uses a laser, emits an input beam (12) which is comprised of two linear orthogonally polarized components as indicated by the dot and arrow, which may or may not be of the same optical frequency. If the frequencies are the same, see for example, Downs et al., U.S. Pat. No. 4,360,271 issued Nov. 23, 1982. If the frequencies are different, see for example, Bagley et al., U.S. Pat. No. 3,458,259 issued July 26, 1969 and commonly owned, copending U.S. patent applications Ser. Nos. 710,859, entitled "Apparatus to Transform a Single Frequency, Linearly Polarized Laser Beam into a Beam with Two, Orthogonally Polarized Frequencies", filed Mar. 12, 1985; 710,928, entitled "Heterodyne Interferometer System" filed Mar. 12, 1985; and 710,927, entitled "Apparatus to Transform a Single Frequency, Linearly Polarized Laser Beam into a High Efficiency Beam with Two, Orthogonally Polarized Frequencies," filed Mar. 12, 1985 all of which are specifically incorporated by reference herein in their entirety, in which instance source (10) would provide an electrical reference signal (11), shown by dotted lines in FIG. 1, which would correspond to the frequency difference between the two stabilized frequencies. No such reference signal (11) is provided when the two linear orthogonally polarized components comprising the input beam (12) are of the same optical frequency.

Beam (12) is incident on a tilted parallel plate (16) which is preferably a tilted glass substrate with optically flat surfaces (17) and (18) which are mutually parallel. The function of the tilted parallel plate (16) is to spatially separate the two polarization components using conventional polarization techniques. Beam (12) passes through surface (17) to become beam (13) which has the same polarization as beam (12). Surface (17) has an antireflection coating (21A) over the region where beam (12) passes through it. Polarization coating (23A) on surface (18) splits beam (13) so that one polarized component is transmitted as beam (30) whereas the other orthogonally polarized component is reflected as beam (14). Beam (14) is totally reflected from reflective coating (25A) on surface (17) to become beam (15). Beam (15) passes through surface (18) to become beam (31) which has the same polarization as beam (15). Surface (18) has an antireflection coating (27A) over the region where beam (15) passes through it. Beam (31) passes through half-wave phase retardation plate (29A) which rotates the linear polarization of beam (31) by 90° so that the resultant beam (33) has the same polarization as beam (30). Beams (30) and (33) enter polarizing beamsplitter (40), which has a polarization coating (42) and are transmitted as beams (34) and (35), respectively. Beams (34) and (35) then pass through quarter-wave phase retardation plate (44) and are converted into circularly polarized beams (50) and (51) respectively.

Beams (50) and (51) are incident on refractive index cell (78) which is preferably comprised of two optical windows (70) and (75) affixed to ends of a cylinder (73) to form a sealed volume (74) which is evacuated, or in some instances filled with a gas. Windows (70) and (75) and cylinder (73) are preferably made of the same low expansion transparent material, e.g. quartz. The surfaces (71) and (72) of window (70) are preferably coated with an antireflection coating, and surface (76) of window (75) is preferably coated with a high reflectivity coating, thus making window (75) effectively a mirror.

Beams (50) and (51) pass through window (70) unaffected to become beams (50A) and (51A), respectively. Beam (50A) is in the ambient air (77) whose refractive index changes are to be measured, while beam (51A) is within the sealed volume (74) whose refractive index is either identically equal to one if it is evacuated, or to a constant (but unknown) value if it is filled with a gas. Beams (50A) and (51A) are reflected from surface (76) as beams (50B) and (51B) and pass back through window (70) as beams (50C) and (51C), respectively. Beams (50C) and (51C) then pass back through quarter-wave phase retardation plate (44) and are converted back into linearly polarized beams which are orthogonally polarized to the original incident beams (34) and (35). Beams (50C) and (51C) are reflected by polarization coating (42) to become beams (52) and (53). Beams (52) and (53) are reflected by retroreflector (45) to become beams (54) and (55). Beams (54) and (55) are reflected by polarization coating (42) to become beams (56) and (57). Beams (56) and (57) pass through quarter-wave phase retardation plate (44) and are converted into circularly polarized beams (58) and (59). Beams (58) and (59) pass through window (70) to become beams (58A) and (59A) respectively. Beam (58A) like beam (50A), is in the ambient air (77), while beam (59A), like beam (51A), is within sealed volume (74). Beams (58A) and (59A) are reflected from surface (76) as beams (58B) and (59B) and pass back through window (70) as beams (58C) and (59C), respectively. Beams (58C) and (59C) are transmitted by polarization coating (42) and leave polarizing beamsplitter (40) as beams (60) and (63). Beams (60) and (63) are mutually parallel by virtue of the inherent optical properties of retroreflector (45), independent of any tilt that may be present in window (75). Beam (60) passes through half-wave phase retardation plate (29B) which preferably rotates the linear polarization of beam (60) by 90° so that the resultant beam (62) has a linear polarization which is orthogonal to beam (63). Beam (62) passes through surface (18) to become beam (64) which has the same polarization as beam (62). Surface (18) has an antireflection coating (27B) over the region where beam (62) passes through it. Beam (64) is totally reflected from reflective coating (25B) to become beam (65). Surface (17) has reflective coating (25B) over the region where beam (64) intersects it. Beam (65) and (63) are recombined to form beam (66) by polarization coating (23B) on surface (18) where beams (65) and (63) intersect. Beam (66) passes through surface (17) to become beam (80). Surface (17) has an antireflection coating (21B) over the region where beam (66) passes through it.

Beam (80), like input beam (12), has two orthogonally polarized components. Each component has traversed exactly the same optical path length (through air and glass) except for the optical path difference in refractive index cell (78). The optical path difference, OPD, is given by $$OPD = 4L(n - n_o),$$

where L is the predetermined separation between windows (70) and (75), $n_o$ is the refractive index of sealed volume (74) ($n_o = 1$ if evacuated), and n is the refractive index of ambient air (77). The optical path difference results in a phase difference, $\delta$, between the two polarization components of beam (80) given by $$\delta = 2\pi OPD/\lambda$$

$$\delta = 8\pi L(n - n_o)/\lambda,$$

where $\lambda$ is the wavelength of source (10). Changes in the refractive index, n, of ambient air (77) cause this phase difference to vary. This phase variation, $\Delta\delta$, is given by $$\Delta\delta = 8\pi L\Delta n/\lambda.$$

Therefore, changes in the refractive index, n, of ambient air (77) is expressed as, $$\Delta n = (\lambda/8\pi L)\Delta\delta.$$

The phase variation, $\Delta\delta$, is measured by passing beam (80) through polarizer (81), oriented at 45° to each polarization component, which mixes the two orthogonally polarized components in beam (80) to give beam (82). The interference between the two polarization components is detected by photodetector (83) producing electrical signal (85). Electronic module (90) extracts the phase variation from electrical signal (85). When the two polarization components of beam (12) are of the same optical frequency, module (90) does not require reference signal (11) since there is no corresponding frequency difference, and conventionaly extracts the phase variation from signal (85) such as in the manner described in U.S. Pat. No. 4,360,271. However, when the two polarization components of beam (12) are of different frequencies, an additional sinusoidal electrical reference signal (11) equal in frequency to the difference between the two optical frequencies is required by electronic module (90), which reference signal (11), as previously mentioned, would be provided from source (10). In such an instance, photodetector (83) would detect the interference between the two frequency components as a sinusoidal intensity variation with a frequency approximately equal to the difference frequency between the two components of beam (12), such as explained in my copending U.S. patent application Ser. No. 810,999, the contents of which are specifically incorporated by reference herein in their entirety, and module (90) would preferably comprise a phase meter/accumulator such as described in the aforementioned copending U.S. patent application Ser. No. 710,928. In either event, electronic module (90) provides output (92) which is a direct measurement of the phase variation, and thus directly proportional to the change in refractive index of ambient air (77) as expressed in the previously described equations.

This optical configuration is extremely insensitive to measurement error because changes in the other optical components, such as those induced mechanically or thermally, affect both polarization components equally and, therefore, have no influence on the measured phase variation (92).

While FIG. 1 depicts an embodiment of the instant invention where all of the optical beams are in a single plane, clearly modifications using multiple planes can be made without departing from the scope of the invention as defined in the following claims.

Figure 2:
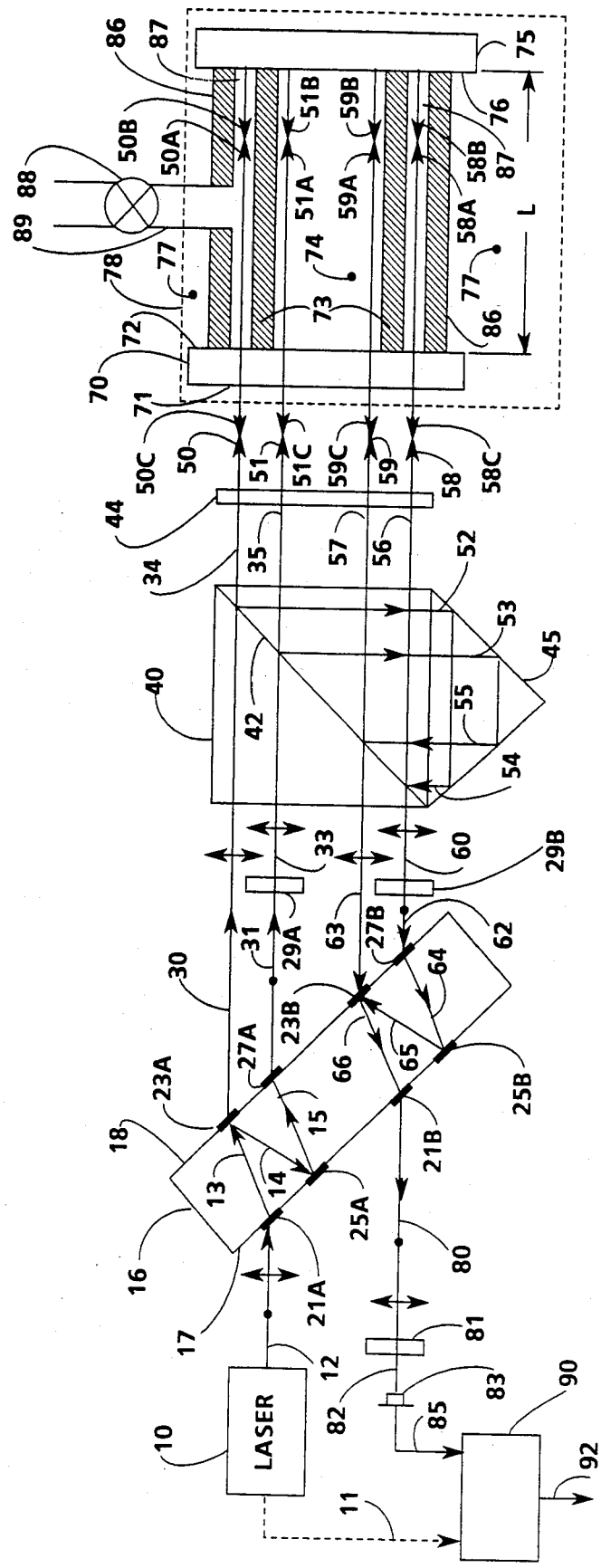

Referring now to FIG. 2, FIG. 2 depicts in schematic form a second embodiment of the instant invention in which the refractive index cell (78) is preferably configured to measure the absolute refractive index of a gas. Like reference numerals are used in FIG. 2 for like elements previously described with reference to FIG. 1. The modification to the embodiment of FIG. 1 exists in the area of the refractive index cell (78) which is now preferably comprised of two concentric tubes (73) and (86) which have the window (70) affixed to one end of each tube and the window or mirror (75) affixed to each of the other tube ends to provide two sealed volumes, namely (74) and (87). Once again the sealed volume (74) is evacuated so that $n_o = 1.0$. The volume (87) is preferably connected to a vacuum pump (not shown) or to the supply of the gas to be measured using connecting pipe (89) and valve (88). The volume (87) is initially evacuated so that the initial value of the phase variation between the reference and measurement beams is zero, i.e. the optical path difference is zero. The gas to be measured is preferably allowed to slowly enter the volume (87).

Under these conditions the phase variation, $\Delta\delta$, is given by $$\Delta\delta = 8\pi L(n-1)\lambda$$

so that the absolute refractive index is given by $$n = 1 + (\lambda/8\pi L)\Delta\delta.$$

The remainder of the embodiment depicted in FIG. 2 is preferably the same as described in the description of FIG. 1 and will not be described again.

Some of the principal advantages of the instant invention are: (1) increased measurement accuracy, (2) the length, L, need not be known with extreme accuracy; (3) small variations in the length, L, during a measurement are tolerable; and (4) the air around the refractive index cell truly represents the ambient environment.

While a preferred embodiment of the invention has been disclosed, obvious modifications can be made therein, without departing from the scope of the invention as defined in the following claims.

What is claimed is:

1. An apparatus for the measurement of the refractive index of a gas comprising a differential plane mirror interferometer means for producing a pair of measurement beams and a pair of reference beams from an input beam having a pair or orthogonally polarized components; a gas-tight refractive index cell means comprised of a first hollow cylindrical tube member, a window affixed to a first end of said first tube and a mirror affixed to the opposite end of said first tube, said window, mirror and tube interior comprising a first sealed volume, said gas to be measured surrounding said first tube in said cell means, said cell means being optically aligned with said interferometer means for enabling said pair of reference beams produced by said interferometer means to pass inside of said first sealed volume and said pair of measurement beams produced by said interferometer means to pass outside of said first tube in said gas surrounding said first tube and back to said interferometer means after said measurement beams and said reference beams traverse said cell means; said window being affixed to said first end closest to said interferometer means; said interferometer means producing an output beam having a pair of orthogonally polarized components from said beams which have traversed said cell means, said output beam components traversing the same optical path length except for the optical path difference in said cell means; means optically aligned with said interferometer means output beam for receiving said beam and measuring any phase variation between said output beam components; and means operatively connected to said phase variation measuring means for converting said measured phase variation into an output signal representing the refractive index parameter being measured.

2. An apparatus in accordance with claim 1 wherein said cell means comprises a single sealed volume, said refractive index parameter comprising any changes in the refractive index of said gas.

3. An apparatus in accordance with claim 2 wherein said gas is ambient air.

4. An apparatus in accordance with claim 3 wherein said sealed volume is evacuated and has a refractive index of 1.

5. An apparatus in accordance with claim 3 wherein said sealed volume is filled with a gas having a refractive index which is a constant.

6. An apparatus in accordance with claim 2 wherein said sealed volume is evacuated and has a refractive index of 1.

7. An apparatus in accordance with claim 2 wherein said sealed volume is filled with a gas having a refractive index which is a constant.

8. An apparatus in accordance with claim 1 wherein said gas is ambient air.

9. An apparatus in accordance with claim 8 wherein said sealed volume is evacuated and has a refractive index of 1.

10. An apparatus in accordance with claim 8 wherein said sealed volume is filled with a gas having a refractive index which is a constant.

11. An apparatus in accordance with claim 8 wherein said optical path difference OPD in said cell means is defined by the expression $OPD=4L(n-n_o)$ where L is the predetermined separation between said window and said mirror, $n_o$ is the refractive index of said sealed volume and n is the refractive index of said gas surrounding said first tube.

12. An apparatus in accordance with claim 11 wherein said interferometer means comprises a laser source said phase variation $\Delta\delta$ is a measure of a phase difference $\delta$ between said output beam components as a result of said optical path difference given by the expression $\delta=8\pi L(n-n_o)/\lambda$, wherein $\lambda$ is the wavelength of said laser source.

13. An apparatus in accordance with claim 12 wherein changes in said refractive index n of said surrounding gas cause said phase difference $\delta$ to vary to provide said phase variation $\Delta\delta$ in accordance with the expression $\Delta\delta=8\pi L\Delta n/\lambda$, changes in the refractive index n of said surrounding gas being defined by the expression $\Delta n=(\lambda/8\pi L)\Delta\delta$.

14. An apparatus in accordance with claim 13 wherein said sealed volume is evacuated and has a refractive index of 1.

15. An apparatus in accordance with claim 14 wherein said cell means comprises a single sealed volume, said refractive index parameter comprising any changes in the refractive index of said gas.

16. An apparatus in accordance with claim 15 wherein said interferometer means comprises a single laser source, said input beam comprising a laser beam.

17. An apparatus in accordance with claim 16 wherein said interferometer means further comprises a tilted glass substrate having mutually parallel optically flat surfaces optically aligned with said laser input beam for spatially separating said polarization components of said input beam.

18. An apparatus in accordance with claim 17 wherein said interferometer means further comprises a polarizing beamsplitter optically disposed between said tilted glass substrate and said cell means.

19. An apparatus in accordance with claim 1 wherein said sealed volume is evacuated and has a refractive index of 1.

20. An apparatus in accordance with claim 1 wherein said sealed volume is filled with a gas having a refractive index which is a constant.

21. An apparatus in accordance with claim 1 wherein said optical path difference OPD in said cell means is defined by the expression $OPD=4L(n-n_o)$ where L is the predetermined separation between said window and said mirror, $n_o$ is the refractive index of said sealed volume and n is the refractive index of said gas surrounding said first tube.

22. An apparatus in accordance with claim 21 wherein said interferometer means comprises a laser source said phase variation $\Delta\delta$ is a measure of a phase difference $\delta$ between said output beam components as a result of said optical path difference given by the expression $\delta=8\pi L(n-n_o)/\lambda$, wherein $\lambda$ is the wavelength of said laser source.

23. An apparatus in accordance with claim 22 wherein changes in said refractive index n of said surrounding gas cause said phase difference $\delta$ to vary to provide said phase variation $\Delta\delta$ in accordance with the expression $\Delta\delta=8\pi L\Delta n/\lambda$, changes in the refractive index n of said surrounding gas being defined by the expression $\Delta n=(\lambda/8\pi L)\Delta\delta$.

24. An apparatus in accordance with claim 1 wherein said interferometer means comprises a single laser source, said input beam comprising a laser beam.

25. An apparatus in accordance with claim 24 wherein said interferometer means further comprises a tilted glass substrate having mutually parallel optically flat surfaces optically aligned with said laser input beam for spatially separating said polarization components of said input beam.

26. An apparatus in accordance with claim 25 wherein said interferometer means further comprises a polarizing beamsplitter optically disposed between said tilted glass substrate and said cell means.

27. An apparatus in accordance with claim 1 wherein said cell means further comprises a second hollow cylindrical tube member disposed between said window and said mirror and concentric to said first tube member and spaced therefrom to define a second sealed volume, said gas to be measured being contained in said second sealed volume, said cell means further comprising valve means for controlling the entry of said gas to be measured into said second sealed volume, said parameter to be measured comprising the absolute refractive index of said gas.

28. An apparatus in accordance with claim 27 wherein said first sealed volume is evacuated.

29. An apparatus in accordance with claim 28 wherein said interferometer means comprises a laser source, said second sealed volume being initially evacuated for providing an initial phase variation value of zero between said reference and said measurement beams for providing an optical path difference of zero, said gas thereafter controllably entering said second sealed volume through said valve means for providing a phase variation $\Delta\delta'$ defined by the expression $\Delta\delta = 8\pi L(n-1)/\lambda$, where $\lambda$ is the wavelength of said laser source, L is the predetermined separation between said window and said mirror, and n is the absolute refractive index of said gas to be measured, n being defined by the expression $n = 1 + (8\pi L)\Delta\delta$.

30. An apparatus in accordance with claim 29 wherein said interferometer means comprises a single laser source, said input beam comprising a laser beam.

31. An apparatus in accordance with claim 30 wherein said interferometer means further comprises a tilted glass substrate having mutually parallel optically flat surfaces optically aligned with said laser input beam for spatially separating said polarization components of said input beam.

32. An apparatus in accordance with claim 31 wherein said interferometer means further comprises a polarizing beamsplitter optically disposed between said tilted glass substrate and said cell means.

33. An apparatus in accordance with claim 27 wherein said interferometer means comprises a single laser source, said input beam comprising a laser beam.

34. An apparatus in accordance with claim 33 wherein said interferometer means further comprises a tilted glass substrate having mutually parallel optically flat surfaces optically aligned with said laser input beam for spatially separating said polarization components of said input beam.

35. An apparatus in accordance with claim 34 wherein said interferometer means further comprises a polarizing beamsplitter optically disposed between said tilted glass substrate and said cell means.

* * * * *